United States Patent [19]

Nichols et al.

[11] Patent Number: 5,433,708

[45] Date of Patent: Jul. 18, 1995

[54] METHOD AND DEVICE FOR THERMAL ABLATION HAVING IMPROVED HEAT TRANSFER

[75] Inventors: Colin J. Nichols, Fremont; William R. Dubrul, Redwood City; Robert S. Behl, Palo Alto, all of Calif.

[73] Assignee: Innerdyne, Inc., Sunnyvale, Calif.

[21] Appl. No.: 73,639

[22] Filed: Jun. 7, 1993

Related U.S. Application Data

[63] Continuation of Ser. No. 702,796, May 17, 1991, abandoned.

[51] Int. Cl.⁶ .......................... A61F 7/00; A61B 17/36
[52] U.S. Cl. ...................................... 604/113; 606/27; 606/30
[58] Field of Search .................... 606/27–31; 604/113, 114; 607/96, 104–107, 138

[56] References Cited

U.S. PATENT DOCUMENTS

| | | | |
|---|---|---|---|
| 2,512,226 | 6/1950 | Edwards | 392/304 |
| 3,901,224 | 8/1975 | Bucalo . | |
| 3,934,117 | 1/1976 | Schladitz | 392/480 |

(List continued on next page.)

FOREIGN PATENT DOCUMENTS

| | | | |
|---|---|---|---|
| 71786/87 | 10/1988 | Australia . | |
| 3725691 | 3/1988 | Germany . | |
| 1143149 | 2/1969 | United Kingdom | 128/401 |
| 1329781A | 8/1957 | U.S.S.R. . | |
| 281489 | 9/1970 | U.S.S.R. . | |
| 8103616 | 12/1981 | WIPO | 128/401 |

OTHER PUBLICATIONS

Coleman, "Non–Surgical Ablation of the Gallbladder," Proc. 1988 SCVIR, pp. 214–219.
Salomonowitz et al. (1984) Arch. Surg. 119:725–729.
Getrajdman et al. (1985) Invest. Radiol. 20:393–398.
Getrajdman et al. (1986) Invest. Radiol. 21:400–403.
Remley et al. (1986) Invest. Radiol. 21:396–399.
Becker et al. (1988) Radiology 167:63–68.
Becker et al. (1989) Radiology 171:235–240.
Becker et al. (1989) Work in Progress Paper #1354, RSNA Meeting, Nov.
Neuwirth et al., The Endometrial Ablator: A New Instrument, Obs. & Gyn., vol. 83, No. 5, Part 1, May 1994, pp. 792–796.
McGahan et al., Refinement of a Technique for a Thermocholec . . . Inves. Rad., vol. 29, No. 3, pp. 355–360.
Yedlicka et al., Thermal Ablation of the Gallbladder, Jor. of Vasc. & Intrvd. Rad., vol. 4, No. 3, May–Jun. '93, pp. 367–371.
McGahan et al., New Method for Thermocholecystectomy—Initial Experience . . . , Inves. Rad., vol. 27, Nov. 1992, pp. 947–953.
Coleman et al., Thermal Ablation of the Gallbaldder, Radiology, vol. 180, No. 2, Aug. 1991, pp. 363–366.

*Primary Examiner*—Stephen C. Pellegrino
*Assistant Examiner*—Nancy Mulcare
*Attorney, Agent, or Firm*—Townsend and Townsend Khourie and Crew

[57] ABSTRACT

A thermal ablation catheter includes an elongate body member having a heating element disposed over a predetermined length of its distal end. The heating element is suspended away from an exterior surface of the elongate member to form a circulation region thereunder. Thermally conductive fluid can be introduced through a lumen in the elongate member and distributed within the circulation region to improve heat transfer. The catheter is used to introduce the thermally conductive medium to a hollow body organ where the heating element raises the temperature of the medium sufficiently to induce injury to the lining of the organ. Optionally, an introducer sheath having an expandable cage at its distal end may be used in combination with a thermal ablation catheter. The expandable cage helps center the heating element on the catheter within the body organ and prevents direct contact between the heating element and the wall of the organ. Heat transfer and temperature uniformity can be enhanced by inducing an oscillatory flow of the heat transfer medium through the catheter while heat is being applied.

60 Claims, 4 Drawing Sheets

U.S. PATENT DOCUMENTS

| | | | |
|---|---|---|---|
| 4,160,455 | 7/1979 | Law . | |
| 4,375,220 | 3/1983 | Matvias . | |
| 4,430,076 | 2/1984 | Harris | 604/96 |
| 4,469,103 | 9/1984 | Barrett . | |
| 4,495,990 | 1/1985 | Titus et al. | 392/304 |
| 4,590,938 | 5/1986 | Segura et al. . | |
| 4,638,436 | 1/1987 | Badger et al. . | |
| 4,655,744 | 4/1987 | Thistle et al. . | |
| 4,676,258 | 6/1987 | Inokuchi et al. . | |
| 4,709,698 | 12/1987 | Johnston et al. | 606/31 |
| 4,723,941 | 2/1988 | Thistle et al. . | |
| 4,748,979 | 6/1988 | Hershenson | 606/28 |
| 4,755,167 | 7/1988 | Thistle et al. . | |
| 4,758,596 | 7/1988 | Thistle et al. . | |
| 4,793,776 | 12/1988 | Thistle et al. . | |
| 4,869,248 | 9/1989 | Narula . | |
| 4,872,458 | 10/1989 | Kanehira et al. | 128/401 |
| 4,946,440 | 8/1990 | Hall | 606/27 |
| 4,949,718 | 8/1990 | Neuwirth et al. | 606/27 |
| 4,955,377 | 9/1990 | Lennox | 606/27 |
| 4,955,883 | 9/1990 | Nevyas et al. | 606/28 |
| 4,979,948 | 12/1990 | Geddes et al. . | |
| 5,045,056 | 9/1991 | Behl | 604/113 |
| 5,084,044 | 1/1992 | Quint | 606/27 |
| 5,100,388 | 3/1992 | Behl et al. | 604/113 |
| 5,159,925 | 11/1992 | Neuwirth et al. | 606/28 |
| 5,188,602 | 2/1993 | Nichols | 607/105 |
| 5,195,965 | 3/1993 | Shantha | 606/27 |
| 5,222,938 | 6/1993 | Behl | 607/105 |
| 5,242,390 | 9/1993 | Goldrath | 604/55 |
| 5,277,202 | 1/1994 | Stern | 607/98 |

METHOD AND DEVICE FOR THERMAL ABLATION HAVING IMPROVED HEAT TRANSFER

This is a continuation of application Ser. No. 07/702,796 filed May 17, 1991, now abandoned.

BACKGROUND OF THE INVENTION

1. Field of the Invention

The present invention relates generally to methods and apparatus for the thermal ablation of hollow body organs, such as the gallbladder. In particular, the present invention relates to a catheter structure having a suspended heating element at its distal end and a method for inducing an oscillating flow of a heat transfer fluid past the heating element to enhance heat transfer to and temperature uniformity throughout the transfer medium.

In recent years, a variety of "minimally invasive" surgical procedures has been developed as alternatives to conventional "open" surgery. While minimally invasive surgical procedures have no fixed definition, they are generally characterized by use of specialized surgical tools in combination with visual or radiographic imaging techniques. The specialized tool is generally inserted through an open body orifice or a small surgical incision, and the tool is then positioned within the body using the imaging technique to allow manipulation of the organ or structure to be treated. A common example of least-invasive surgery is arthroscopic knee surgery, where penetration of the surgical tools is minimal. Less-accessible body organs, such as the heart and interior blood vessels, may be reached by specialized catheters which may be routed through the vascular system over relatively long distances. Exemplary of such vascular catheters are balloon dilatation catheters which are used to expand regions of stenosis within diseased blood vessels.

Of particular interest to the present invention are least-invasive surgical techniques which rely on a catheter to deliver heat to the interior of a hollow body organ. As described in detail in co-pending applications Ser. Nos. 07/407,839; 07/529,077; and 07/551,971, the delivery of heat maybe used for deactivating or ablating a diseased body organ, such as a gallbladder, appendix, uterus, kidney, or the like, as well as for blocking other body lumens, such as blood vessels. In each case, the heat is usually delivered by conduction through a thermal conduction medium from a heating element disposed in the organ or blood vessel. The heat destroys the mucosa or endothelial lining of the organ or vessel, resulting eventually in deactivation and eventual resorption of the organ or vessel.

The use of catheters having heating elements to deliver heat within a hollow body organ can be problematic in certain respects. First, heat distribution through the thermally conductive medium can be non-uniform, requiring an increase in the total amount of heat delivered in order to assure that the temperature of all portions of the mucosa are raised above the threshold level necessary to induce injury and necrosis. Such an increase in heat delivery, however, may raise the temperature of the other portions of the mucosa above a desired maximum. Such excessive heating can result in injury to adjacent body organs. A related difficulty arises from the limited heat transfer capacity of the thermally-conductive medium. In order to deliver sufficient heat to remote portions of the mucosal wall, it may be necessary to raise the surface temperature of the heating element above a desired maximum. Excessively hot heating surfaces can result in fouling of the heating element as a result of coagulation and denaturing of blood and other proteins present. Such fouling, of course, further reduces the heat transfer capacity of the heating element.

For these reasons, it would be desirable to provide improved methods and apparatus for delivering heat to the interior of hollow body organs. It would be particularly desirable to provide thermal ablation catheters having improved heat transfer characteristics so that the surface temperature of a heating element can be maintained below a desired maximum level, typically being below about 100° C., preferably being below about 90° C. The methods and apparatus should further provide for improved uniformity of heat distribution throughout the thermally conductive medium used to transfer heat from the catheter to the mucosal lining of the hollow body organ. Such improved heat transfer should even further reduce the surface temperature of the heating element as well as reducing the total amount of heat delivered to the body organ. The reduction in total heat will reduce the likelihood of unintentionally injuring adjacent body organs. The catheters of the present invention should have few or no moving parts and should be simple and reliable in design.

2. Description of the Background Art

U.S. Pat. No. 4,160,455, describes a bidirectional pump and unidirectional valve means for circulating a fluid through a housing containing a heating element. The entire housing is placed within a body cavity for effecting heat treatment of tumors. The device relies on forming a single high-speed outlet jet to agitate the fluid content of the organ. U.S. Pat. No. 4,979,948, describes a device having a radio frequency balloon electrode at its distal end for thermally destroying the mucosal layer of a body organ, such as the gallbladder. U.S. Pat. Nos. 4,655,744; 4,723,941; 4,755,167; 4,758,596; 4,793,776; and Australian published application A-71786/87, describe improved methods for performing chemical cholecystectomy where a stone dissolving agent is oscillated in and out of a body area.

Coleman, *Non-Surgical Ablation of the Gallbladder,* Proc. 1988 SCVIR, pp 214–219, is a review article discussing various techniques for non-surgical gallbladder ablation, including the work of Salomonowitz and of Getrajdman relating to the introduction of an externally heated medium to induce fibrosis of the gallbladder. The article further presents data demonstrating thermal ablation of a dog's gallbladder after open surgical injection of hot contrast media. The work of Salomonowitz is described in Salomonowitz et al. (1984) Arch. Surg. 119:725–729. The work of Getrajdman is described in Getrajdman et al. (1985) Invest. Radiol. 20:393–398 and Getrajdman et al. (1986) Invest. Radiol. 21:400–403. The use of sclerosing agents to induce gallbladder fibrosis is described in Remley et al. (1986) Invest. Radiol. 21:396–399. See also Becker et al. (1988) Radiology 167:63–68; Becker et al. (1989) Radiology 171:235–240; and Becker et al. (1989) Work in Progress Paper #1354, RSNA Meeting, November 1989. U.S. Pat. No. 4,160,455, describes a device for internally heating a body cavity for therapy, where the heat is intended to inhibit the growth of tumor cells. German Patent 37 25 691 describes a catheter combining a heater at its distal tip and a balloon proximate the heater, where the heater is not directly exposed to the fluid environment surrounding the catheter tip. U.S. Pat. No. 4,869,248, describes a thermal ablation catheter having a resistive heating loop at its distal end. Other patent documents describing heated or cooled catheters include U.S. Pat. Nos. 4,676,258; 4,638,436; 4,469,103; 4,375,220; 3,901,224; USSR 1329-781-A; and USSR 281489.

The subject matter of the present application is related to that of co-pending application Ser. Nos. 07/407,839; 07/529,077; and 07/551,971, assigned to the assignee of the present application, the disclosures of which are incorporated herein by reference.

SUMMARY OF THE INVENTION

The present invention comprises an apparatus and method for thermally ablating a hollow body organ, such as a gallbladder, uterus, appendix, kidney, and the like. The apparatus comprises an elongate member having a heating element at its distal end. The heating element is suspended away from the surface of the distal end of the elongate member, and a means is provided for distributing a heat transfer fluid to a circulation region defined between the heating element and the surface (and extending into the space between adjacent turns of a coiled heating element as described hereinafter). In this way, heat transfer to the medium is improved as the fluid is introduced through the catheter. The method of the present invention further enhances heat transfer and uniform temperature distribution by providing for an oscillatory flow of heat transfer fluid through the heating element during a portion of or all of the thermal ablation procedure.

In a preferred aspect, the heating element of the catheter is a coil wrapped over three or more axial ribs formed at the distal end of the elongate member. The individual windings of the coil are usually spaced-apart, preferably by from 0.5 to 2 diameters, in order to permit flow of heat transfer fluid therethrough. Other heating element designs, such as perforate electrodes, meshes, or the like, would also be possible.

In a second specific aspect, the catheter is provided as part of a thermal ablation system which also includes a power supply and a means for inducing oscillatory flow of the thermally conductive medium through the catheter. Optionally, the system may further include an introducer sheath having an expandable cage at its distal end, where the cage may be expanded within the hollow body organ to open its interior to permit optimal positioning of the heating element of the catheter. For example, the introducer sheath may position the heating element substantially at the center of the hollow body organ in order to enhance uniform temperature distribution to all portions of the mucosal lining.

The method of the present invention comprises percutaneously introducing the catheter so that the heating element is within the interior of the hollow body organ, optionally using an introducer sheath having an expandable cage as described above. The thermally conductive medium is then introduced through the catheter so that it is unconstricted as it enters the hollow body organ. The thermally conductive medium is heated by inducing an oscillatory flow through the circulation region and heater of the catheter. The oscillatory flow comprises alternately aspirating and expelling relatively small volumes of the thermally conductive medium through the catheter, typically in the range from about 0.1 ml to 3 ml. The oscillation will typically be performed at from about 0.1 Hz to 5 Hz with the temperature of the bulk medium being maintained in the range from about 50° C. to 60° C. The surface temperature of the heating element will usually be between about 70° C. and 90° C., with the minimum differential temperature between the element and medium being possible because of both the element design and oscillatory flow.

The present invention provides the combined advantages of a catheter construction having improved heat transfer and a catheter system and method having improved mixing of the thermally conductive medium to enhance both heat transfer and uniformity of temperature distribution. In this way, the surface temperature of the heating element can be reduced while maintaining a desired heat flux to the mucosal or other lining of the hollow body organ. In addition, because of the uniform temperature distribution, the total amount of heat flux delivered to the hollow body organ can be reduced. This is desirable since it reduces the risk of injury to adjacent body organs. These and other advantages will be described more fully in connection with the detailed description of the drawing which follows.

DESCRIPTION OF THE SPECIFIC EMBODIMENTS

According to the present invention, apparatus and methods are provided for heating the interior of a wide variety of hollow body organs, cavities, ducts, and passages, particularly including those which have an endothelial lining, mucous membrane, or other internal surface which may be thermally injured to inactivate the organ and usually to induce necrosis and subsequent fibrosis of the organ itself. Alternatively, the present invention may be used to provide thermal therapy where the temperature of the surrounding tissue is raised, particularly in the treatment of solid tumors and other neoplastic diseases. Exemplary hollow body organs and cavities include the gallbladder, the appendix, the uterus, the kidney, and the like. Exemplary hollow body passages and ducts include blood vessels, fistulas, and the like. When the intent is to inactivate, the hollow body organ will usually be diseased or in some way abnormal prior to treatment according to the present invention. When the desire is to thermally treat surrounding tissue, an organ or passage may serve merely as an access route. In other cases, it may be desirable to ablate and destroy apparently healthy body organs or parts in order to achieve a desired purpose, e.g., blockage of a blood vessel in a varicocele procedure. For convenience hereinafter, the phrase "hollow body organ" is intended to embrace hollow body organs, hollow body passages and hollow body cavities.

The catheter of the present invention comprises an elongate member having proximal and distal ends. The elongate member may be flexible or rigid, although flexible catheters are preferred for most applications. The length of the catheter will vary depending on the application, typically being from about 10 cm to 100 cm, usually from about 10 cm to 50 cm, and more usually from about 10 cm to 30 cm, although longer structures will usually be provided for intravascular applications.

Rigid elongate members may be formed from metals, typically stainless steel, rigid plastics, and the like, while flexible elongate members will typically be formed from extruded organic polymers, such as silicone rubber, polyurethane, polyvinyl chloride, nylon, and the like.

Elongate members will typically include a multiplicity of lumens to provide for fluid communication between the proximal end (which remains outside the patient) to the distal end (present inside the patient during treatment). Normally, a lumen will be provided for delivering and aspirating the thermally conductive medium to the hollow body organ. Additional lumens may be provided for delivery of the catheter over a movable guide wire, for venting the hollow body organ while the thermally conductive medium is being delivered, for electrical power and signal connections, and the like.

A heating means for raising the temperature of the fluid environment surrounding the distal end of the catheter will be provided at or near the distal tip of the elongate member typically being within about 10 cm of the tip, more typically being within about 5 cm. The heating means will provide a heated surface for heating fluid surrounding the catheter tip, usually including a resistive heater element. Preferably, the heated surface of the heating means will be exposed directly to the environment surrounding the catheter, with little or no insulation covering the surface, in order to enhance heat transfer. The heating means will be directly exposed to its surrounding environment and will not be enclosed in a housing or other structure which substantially impedes direct heat exchange with surrounding fluid in the body organ.

The heated surface will be located over an extended axial length at or near the distal tip of the elongated member. The length will usually be from about 1 cm to 8 cm, more usually being about 2 cm to 6 cm, and most usually being about 1.5 to 4 cm. The heated surface will be suspended over or spaced-apart from the exterior surface of the elongate member to define a circulation region therebetween. As described hereinafter, the thermally conductive fluid will usually be passed from the central lumen into the circulation region to enhance heating thereof. In particular, by suspending the heating element, additional heating surface of the element is exposed to the thermally conductive medium as it is distributed from the catheter.

The heating element will be a permeable or perforate structure in order to increase the total surface area to enhance heat transfer. For example, a cylindrical mesh or other perforate cylindrical structure may find use as a heating element, where the thermally conductive fluid can pass through the interstices or apertures of the structure.

A preferred heating element is a coiled structure where an elongate heating element, e.g., a wire, is wrapped in a helix about a supporting structure at the distal end of the elongate member. Successive turns of the helical coil are spaced-apart to permit flow of the thermally conductive medium therethrough and to minimize the thermal effect of adjacent turns on each other. By suspending the heating element away from the elongate member, the exposed surface area of the heating element is maximized, with only the suspension points being blocked. Usually, the heating element will be a resistance heating wire having a diameter in the range from about 0.05 mm to 0.25 mm, usually from about 0.1 mm to 0.15 mm, where spacing between successive windings of the coil are from about 0.5 to 2 diameters. The number of turns in the heating element may vary, typically being from about 3 to 8 turns/mm, more typically being from about 4.5 to 5.5 turns/mm, depending in part on the total length which is to be covered, the linear electrical resistance of the wire, and the desired heat transfer rate.

The means for suspending the heating element from the surface of the elongate member may take a variety of forms. For example, it would be possible to form a plurality of discrete support posts on the surface of the elongate member. Alternatively, the coil heating element could be shaped so that it defines integral support posts in its own structure. Preferably, the suspension means will comprise a plurality of axial ribs formed in the elongate member itself. At least three ribs will be employed, with troughs between adjacent ribs defining the circulation region between the heater and the elongate member. The use of ribs is preferred since they are relatively easy to fabricate, e.g., by extrusion or other techniques.

The thermally conductive medium is introduced through a lumen which extends from the proximal end to distal end of the elongate member. The lumen will open into a plurality of distribution ports at the distal end of the elongate member which permits flow of the thermally conductive medium into and through the recirculation region between the member and the heating element. In this way, heat transfer between the medium being introduced and the heating element can be maximized.

The catheter of the present invention will frequently be employed as part of a thermal ablation system comprising, in addition to the catheter, a power supply connected to the heater and a means for inducing an oscillatory flow of thermally conductive medium past the resistive heating element. The power supply will typically include means for controlling the temperature to which the thermally conductive medium is heated by the heating means. Such a temperature control system may comprise a feedback controller where a temperature sensing element (typically one or more thermocouples or thermistors) is mounted on the catheter and/or an associated introducer sheath (as described in more detail hereinbelow) at a location chosen to accurately measure the heated environment surrounding the catheter, and the energy delivered to the heating means is regulated based on the measured temperature of the medium. Preferably, the temperature control system will include temperature sensing element(s) mounted on an expandable cage at the distal end of the introducer sheath. Such element(s) will be in close proximity to the wall of the organ or duct which is being treated, where the temperature is most critical.

The means for inducing an oscillatory flow of thermally conductive medium will typically include a syringe or other pump mechanism which can be connected to the medium introduction lumen in the catheter. Thus by driving the syringe or pump with a preselected stroke and frequency, a desired volume of the thermally conductive medium can be caused to alternately be aspirated and expelled by the catheter. In this way, heat transfer and uniform heat distribution of the system can be enhanced.

The thermal ablation system optionally includes the introducer sheath having an expandable structure or cage near its distal end. The introducer sheath will be used to introduce the thermal ablation catheter and to expand the portion of the hollow body organ in which the heating element of the catheter is positioned. The expanded cage can thus both protect the organ wall from direct contact with the heating element and position the heating element near the center of the organ so that heat is uniformly distributed to all portions of the organ.

The cage structure on the introducer sheath preferably comprises a plurality of axially aligned fingers which can be introduced in a collapsed configuration and expanded within the hollow body organ or duct in order to provide the desired expanded cage structure. Such a cage, of course, will be substantially open so that the inner wall of the organ or duct will be completely exposed to the thermally conductive medium which is being heated by the catheter. The fingers may be spring-loaded to open when they are released within the body organ or duct, or a separate means may be provided for mechanically causing the opening. Other designs, such as the use of heat memory alloys, may also find use. Regardless of the particular construction, it will be particularly preferred to provide one or more temperature sensing elements on at least some of the finger elements which form the expandable cage. Desirably, the temperature sensing elements will be located at the point(s) of maximum radial expansion on the cage. In this way, the temperature sensing elements will be located immediately adjacent to the inner wall of the hollow body organ during the thermal treatment procedure and will thus be able to accurately measure the localized temperature at the point of thermal impact.

The method of the present invention relies on introducing the thermally conductive medium into the interior of the hollow body organ in such a way that the organ is filled with the medium and the medium is in good thermal contact with substantially the entire interior surface of the organ. The heating element then transfers heat directly to the thermally conductive medium which in turn transfers the heat to the organ wall by convection. In this way, by heating the medium as will be described hereinafter, the temperature of the endothelial lining or mucous membrane of the body organ can be raised to a preselected temperature for a preselected minimum time period in order to permanently injure the lining and deactivate the organ, typically by inducing necrosis. The thermally conductive medium can be virtually any physiologically-compatible liquid, solution, slurry, gel, or the like, which can be percutaneously or directly introduced into the interior of the hollow body organ. Exemplary thermally conductive media include water, normal saline, contrast media, physiological irrigating solution, and the like.

As used herein, the term "ablation" means any injury or damage to the hollow body organ and/or connecting ducts and body passages which results in deactivation of the function of the organ, usually resulting in necrosis and eventual resorption of the organ. The resorption will typically occur over an extended period of weeks, months, or longer.

The thermally conductive medium will usually be introduced to the interior of the hollow body organ at a temperature below that which will have a deleterious effect on the tissue and organs surrounding the hollow body organ being treated. The temperature will be below about 45° C., and more usually being at body temperature (37° C.) or room temperature (about 20° C.). In some cases, however, it may be desirable to introduce the contrast medium above body temperature, usually in the range from about 37° C. to 45° C., in order to shorten the time necessary to raise the temperature of the medium to the treatment temperature, discussed hereinafter.

In order to induce necrosis of the endothelial lining or mucous membrane of the hollow body organ, the temperature of the thermally conductive medium will be raised and maintained above a threshold level which results in injury to the endothelial mucous or membrane. The threshold temperature will generally be above 45° C., usually being in the range from 45° C. to 70° C., more usually being in the range from 50° C. to 65° C., and preferably being in the range from about 53° C. to 60° C. Depending on the precise temperature employed and on the nature of the particular organ being treated, the thermally conductive medium will be maintained above the threshold temperature for a period of time in the range from about 1 to 60 minutes, usually being in the range from about 5 to 40 minutes, and preferably being in the range from about 15 to 35 minutes. Usually, the temperature of the thermally conductive medium will be raised as rapidly as possible and maintained at a substantially constant treatment temperature for the desired treatment period. Alternatively, the treatment temperature may vary or be varied during the treatment period with the total treatment time being adjusted to take the variation in temperature into account.

After the thermally conductive medium has been introduced and heat transfer initiated through the heating element, the method of the present invention relies on alternately aspirating and expelling incremental volumes of the medium through the catheter. Such an oscillatory flow has been found to significantly enhance temperature uniformity (through mixing of the medium) as well as heat transfer (through continuous reversing flow of medium through and past the heating element). Both the enhanced temperature uniformity and the increased heat transfer rate allow the thermal ablation procedures to reduce the total amount of heat delivered to the organ as well as the temperature of the heating surfaces required to deliver that amount of heat.

The volume which is aspirated will usually be substantially the same as the volume which is expelled. Typically, the aspirated and expelled volumes will be in the range from about 0.1 ml to 3 ml, more usually being from about 0.75 ml to 1.5 ml, and the frequency of oscillation will be in the range from about 0.1 Hz to 5 Hz, typically being in the range from about 0.1 Hz to 1 Hz.

After the hollow body organ has been treated with the heated thermally conductive medium at a temperature and for a time sufficient to deactivate the body organ and/or induce necrosis of the endothelial lining or mucous membrane of the organ, the thermal energy being delivered to the medium will be terminated. The thermally conductive medium may then be aspirated from the hollow body organ, typically using the same catheter which was employed to deliver the medium and raise the temperature of the medium as described above. Usually, however, the thermally conductive medium will not be aspirated until the temperature has decreased sufficiently so that its withdrawal will not expose tissues and organs surrounding the catheter to risk. Normally the withdrawal temperature will be below about 45° C., preferably being below about 40° C. Alternatively, the thermally conductive medium can be left within the hollow body organ where it will be resorbed or eliminated by normal physiological processes.

Referring now to FIGS. 1–4, the construction of a catheter 10 constructed in accordance with the principles of the present invention will be described. The catheter 10 includes an elongate element or body 12 having a proximal end 14 and a distal end 16. The catheter body 12 has a cross-sectional profile including three rib elements 18 separated by three trough regions 20. The elongate body 12 further includes four lumens 22, 24, 26, and 28 extending generally from the proximal end 14 to or close to the distal end 16.

Figure 1:
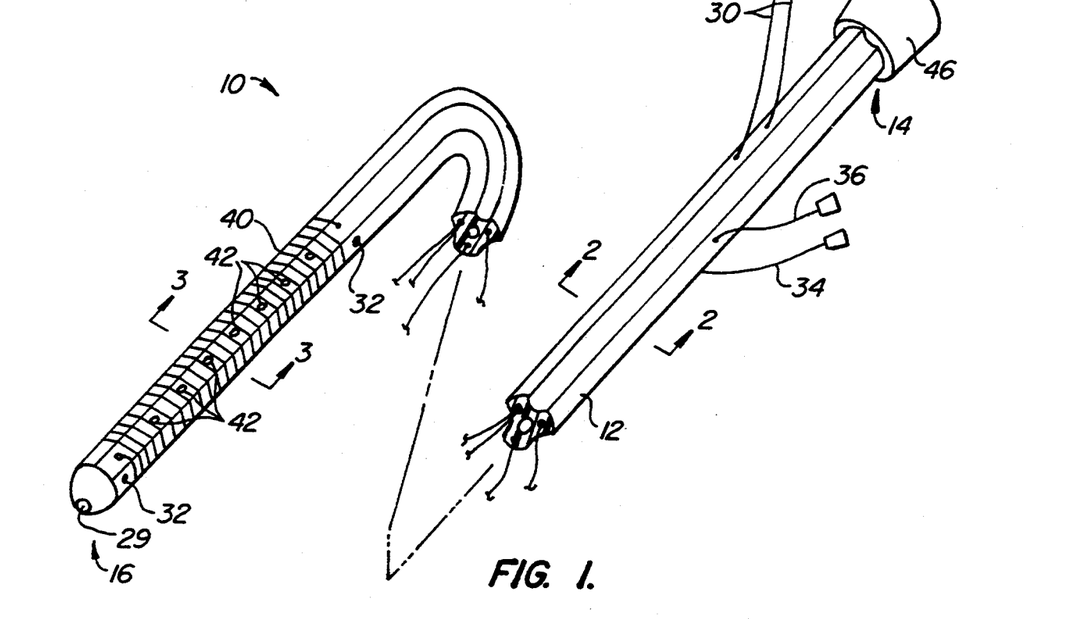
FIG. 1 is perspective view of a thermal ablation catheter constructed in accordance with the principles of the present invention.

The elongate catheter body 12, as illustrated, is shown to be flexible along substantially its entire length. Optionally, portions of the catheter body 12 may be constructed from rigid or semi-rigid materials, for a desired purpose. For example, it may be necessary or desirable to provide a rigid supporting member for the heater having higher or different heat transfer characteristics than the rest of the elongate catheter body. Metals or other heat conductive materials might find use in such designs. Other reasons for departing from the generally flexible nature of the catheter body 12 may occur to those skilled in the art while remaining within the scope of the present invention.

A pair of temperature sensor leads 30 enter the first lumen 22 near the distal end 14 of the catheter body 12 and terminate at external temperature sensors 32 at the distal end 16. Of course, the temperature sensor leads 30 will not be necessary when temperature sensing elements are provided only on the expandable cage of the introducer sheath, as described in more detail hereinafter. Similarly, a first power lead 34 enters lumen 24 at the distal end of the catheter while a second power lead 36 enters lumen 26 at the distal end of the catheter. The power leads 34 and 36 are connected to a heating coil 40 wrapped about and extended axial length near the distal tip of the catheter 10. When not employed for temperature sensor leads, lumen 22 may be used as an auxiliary perfusion and/or aspiration lumen.

Figure 2:
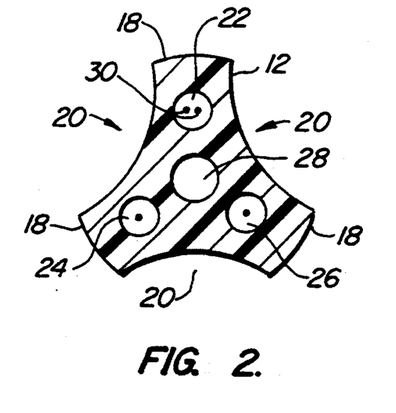
FIG. 2 is a cross-sectional view taken along line 2—2 of FIG. 1.

Central lumen 28 is connected to a plurality of radial apertures 42 which open into the three trough regions 20 which are located beneath the heating coil 40. In this way, the thermally conductive medium can be introduced through a connector 46 at the proximal end of the catheter 10 and in turn be distributed through the various radial apertures 42 which open into a circulation region defined by the trough regions 20 of the catheter body 12. Central lumen 28 terminates in a port 29 located at the distal tip of the catheter body 12. Usually, the diameter of the port 29 will be smaller than that of the lumen 28 so that there will be a close fit about the center wire (not illustrated) which is used for introducing the catheter 10. Such a close fit inhibits flow of the thermally conductive medium through the port 29, which flow is generally undesirable since it bypasses the heating element 40. Flow through the port 29, however, does contribute to the mixing capability of the catheter 10 and to a limited extent may be acceptable or desirable.

Figure 3:
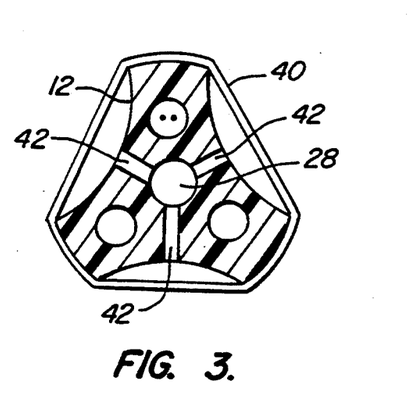
FIG. 3 is a cross-sectional view taken along line 3—3 of FIG. 1.
Figure 4:
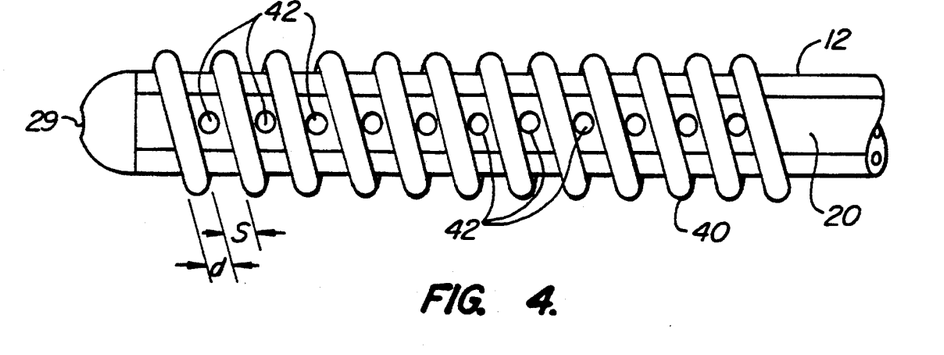
FIG. 4 is a detailed elevational view of the distal end of the catheter of FIG. 1.

Referring now in particular to FIG. 3, the heating coil 40 is wrapped around the catheter body 10 so that it is suspended on the axial ribs 18. Portions of the heating coil 40 which are between the axial ribs 18 are thus completely exposed to the surrounding environment. In particular, the wires are exposed to the thermally conductive medium as it is released or expelled through the axial apertures 42 as well as when it is aspirated back into the catheter through said apertures. Heat transfer or flux from the heating coil 40 will be a compromise between maximizing the total wire length and providing sufficient spacing between adjacent turns of the wire to increase exposure and permit free flow of thermally conductive medium therethrough. That is, the total wire length (which increases the total surface area of the wire) is increased by having a higher number of turns on the catheter. Too high a turn density, however, limits both the effective exposed area of each turn and limits the flow of thermally conductive medium through the coil 40. An optimum compromise heat transfer can be achieved when the spacing s (FIG. 4) between adjacent turns of the coil 40 is equal to from about 0.5 to 2 times the wire diameter d. For catheters having diameters in the range from about 1.5 mm to 3 mm, the wire diameter will usually be in the range from about 0.05 mm to 0.75 mm, with the spacing between adjacent turns of the coil being from about 0.025 mm to 0.25 mm.

Figure 5:
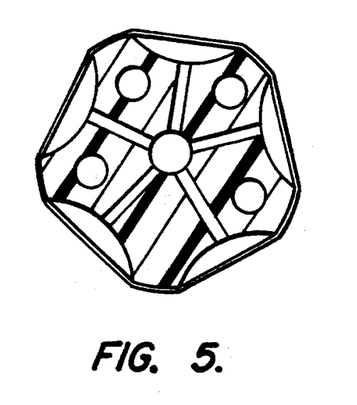
FIGS. 5 and 6 illustrate alternate cross-sections which would be useful in the construction of catheters according to the present invention.
Figure 6:
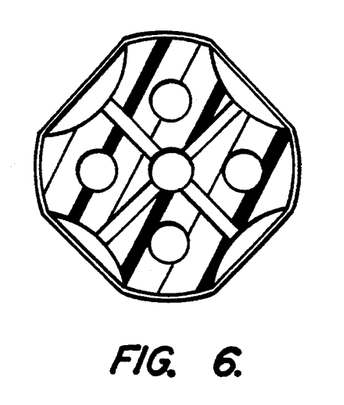

Referring now to FIGS. 5 and 6, alternate catheter body cross sections having different numbers of axial ribs are illustrated. The number of axial ribs is not critical, but it will be appreciated that at least three ribs will usually be required.

Figure 7:
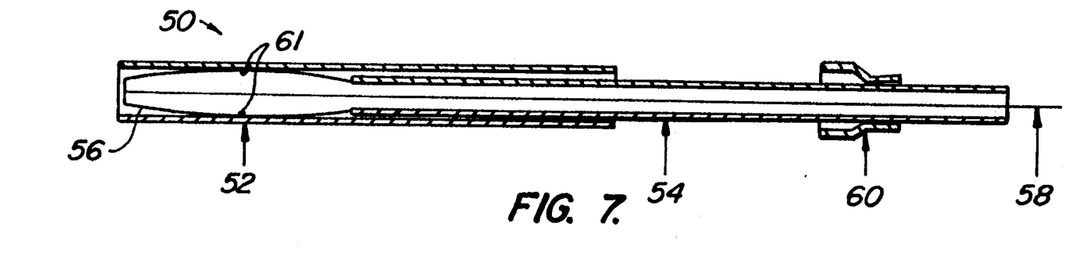
FIG. 7 illustrates an introducer sheath having an expandable cage at its distal end which is useful for introducing the thermal ablation catheter of the present invention, shown with its expandable cage in a collapsed configuration.

Referring now to FIG. 7, an introducer sheath 50 useful for inserting the thermal ablation catheter 10 into a variety of hollow body organs, such as the gallbladder, will be illustrated. The introducer sheath 50 includes an outer sheath member 52 and an inner sheath member 54. The inner sheath member 54 includes an expandable cage 56 at its distal end and a centering wire 58 extending throughout its length. The outer sheath 52 and inner sheath 54 will be configured as nested tubes which are capable of sliding relative to each other. The tubes may be rigid or flexible, usually being flexible to facilitate introduction through relatively tortuous paths.

The cage 56 includes a plurality of resilient fingers 57 (only two are illustrated) which are constrained in a collapsed configuration within the distal end of outer sheath member 52. Usually, although not necessarily, the individual fingers 57 will be connected together at their distal ends so that, when released from the outer sheath 52, they will spring into the expanded configuration illustrated in FIG. 8. It would also be possible to leave the individual fingers 57 unconnected at their distal end so that they remain free to expand away from each other. The cage 56 may also be configured so that it is expanded by pulling proximally on the centering wire 58 to axially compress the cage, forcing its radial expansion. A variety of other specific designs will be apparent to those skilled in the art. It is critical only that the cage 56 be expandable within the target body organ and that, when expanded, it cover or block a minimum area of the inner surface of the body organ.

Figure 8:
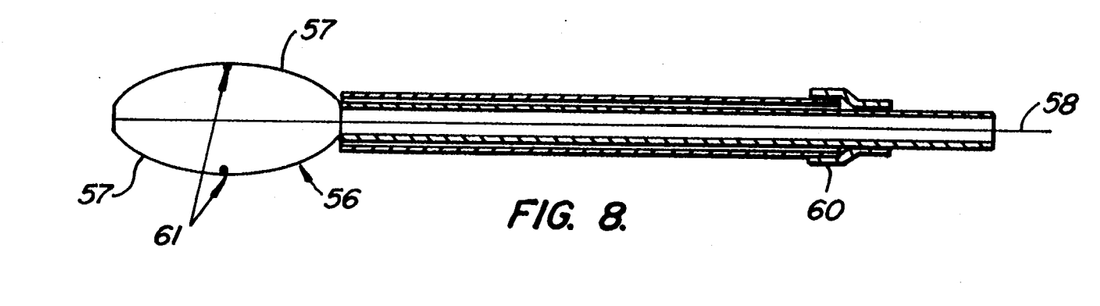
FIG. 8 illustrates the introducer sheath of FIG. 7, shown with its expandable cage in its expanded configuration.

The introducer sheath 50 will be inserted into a hollow body organ, typically through adjacent passages and ducts in a conventional manner, with the expandable cage 56 in a collapsed configuration held within the outer sheath 52. Once the introducer sheath is in position, the outer sheath member 52 will be retracted rearwardly so that the cage 56 is freed to assume its expanded configuration, as illustrated in FIG. 8. Usually, a seal member 60 will be provided to seal against the outer sheath member.

Temperature sensors 61 may be disposed on at least some of the fingers 57 of the expandable cage 56. Preferably, at least two fingers 57 will include at least one temperature sensor 61. More preferably, at least one sensor will be located at the point of maximum expansion as illustrated for sensors 61 in FIGS. 8 and 9. In this way, the temperature sensors 61 will be located immediately adjacent to the endothelium or mucosa of the hollow body organ during treatment.

Figure 9:
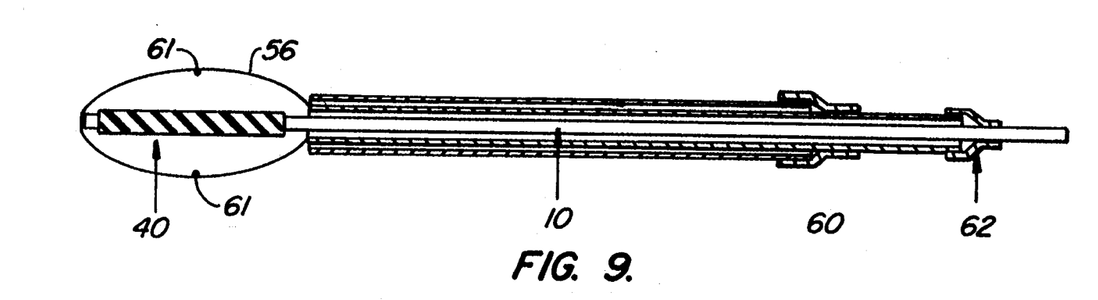
FIG. 9 illustrates the introducer sheath of FIG. 8, shown with the thermal ablation catheter present therein.

Once in position with the cage 56 expanded, the thermal ablation catheter 10 can be introduced over the centering wire 58 so that the heating element 40 is positioned within the expanded cage 56. In this way, the heating element 40 can be optimally positioned within the hollow body organ and direct contact between the heating element and the interior surfaces of the organ prevented. Usually, a second seal 62 will be provided on the catheter 10 in order to seal against the proximal end of the inner sheath 54.

Figure 10:
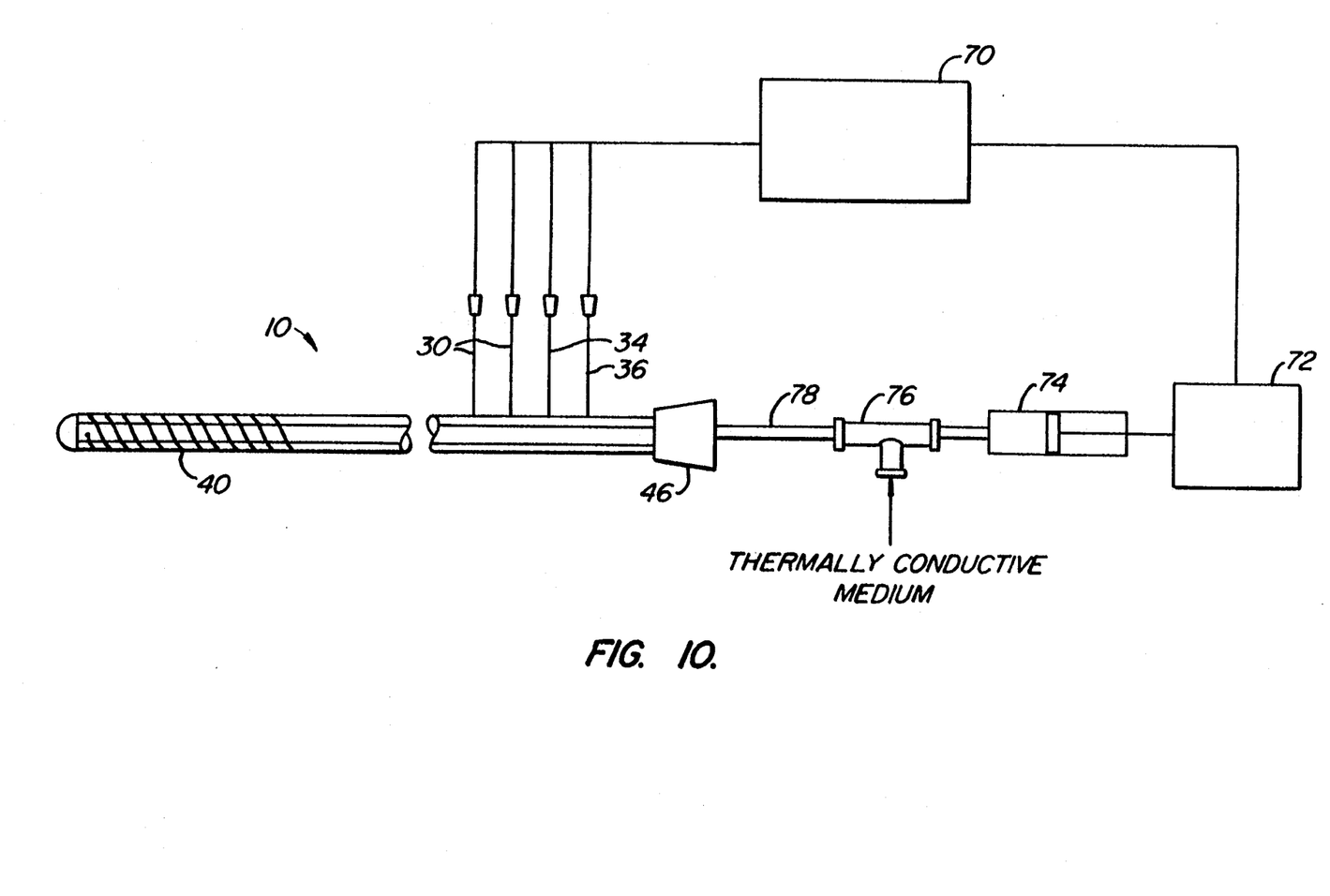

Referring now to FIG. 10, a system for connecting and operating the thermal ablation catheter 10 is illustrated. The system includes a power supply and controller 70 which is connected to the sensor leads 30 and power leads 34 and 36. The power supply and controller may be connected to a mechanical actuator 72 which drives a syringe assembly 74 to create a reciprocating pump mechanism. Alternatively, the mechanical drive may be separately actuated and controlled. The syringe 74, in turn, is connected to a three-way valve 76 which permits the introduction of the thermally conductive medium into connecting tube 78. Connecting tube 78, in turn, is connected to the hub connector 46 on the thermal ablation catheter 10. In this way, after filling the hollow body organ with thermally conductive fluid, the valve 76 can be switched to connect the syringe mechanism 74 and the desired oscillating flow of medium induced by starting the actuator 72. The desired volume, frequency, and the like, can be controlled through the power supply and control system 70 or by independent controls within the actuator 72 itself.

The power to the heating coil 40 will be controlled to achieve a desired temperature, based on the temperature sensors 32 and/or 61. Usually, the fluid temperature will be in the range from about 53° C. to 60° C.

The catheter 10 may be introduced to a hollow body organ, such as the gallbladder, by techniques described in application Ser. Nos. 07/407,839; 07/529,077; and 07/551,971; the disclosures of which have previously been incorporated herein by reference.

For thermal ablation of the gallbladder, the optimum temperature of the medium will be from about 53° C. to 60° C. (usually corresponding to a heating element surface temperature of from about 70° C. to 90° C.), the optimum oscillation frequency will be from about 0.1 Hz to 5 Hz the oscillation volume from about 0.1 ml to 3 ml, and the total treatment time from about 15 minutes to 45 minutes.

Although the foregoing invention has been described in detail for purposes of clarity of understanding, it will be obvious that certain modifications may be practiced within the scope of the appended claims.

What is claimed is:

1. A thermal ablation catheter comprising:
   an elongate member adapted for insertion into a hollow body cavity; said elongate member having a proximal end, a distal end, and a lumen extending between said proximal and distal ends;
   a convective heating element disposed over a predetermined length of the distal end of the elongate member and exposed to an environment external to said catheter;
   means for suspending the heating element away from an exterior surface of the elongate member to form a circulation region between the surface and the heating element; and
   means for distributing a heat transfer fluid from the lumen to the circulation region between the member surface and the heating element, wherein the heating element is capable of heating said heat transfer fluid to a temperature above 45° C.

2. A thermal ablation catheter as is in claim 1, wherein the elongate member is at least partly flexible.

3. A thermal ablation catheter as in claim 1, wherein the heating element is an electrically resistive coil having spaced-apart windings.

4. A thermal ablation catheter as in claim 1, wherein the means for suspending comprises three or more axial ribs formed along the distal end of the elongate member with trough regions between adjacent ribs defining the circulation region.

5. A thermal ablation catheter as in claim 4, wherein the means for distributing a heat transfer fluid comprises a plurality of ports in the elongate member opening into the trough regions.

6. A thermal ablation catheter as in claim 5, wherein the heating element is a coiled wire having a diameter in the range from about 0.05 mm to 0.25 mm, wherein adjacent windings of the coil are spaced-apart by from 0.5 to 2 wire diameters to permit free flow of heat transfer fluid through the heating element.

7. A thermal ablation catheter as in claim 1, further comprising a cage structure surrounding the heating element and means for expanding the cage structure at the distal end of the elongate member.

8. A thermal ablation catheter as in claim 7, wherein the means for expanding a cage is an introducer sheath having a proximal end, a distal end, and the expandable cage at its distal end.

9. A thermal ablation system comprising:
   a catheter including an elongate member having proximal and distal ends an axial lumen, a resistive heating element mounted on an exterior surface over a predetermined length at the distal end of the elongate member, and a plurality of apertures extending radially outward from the axial lumen within the predetermined length of the exterior surface;
   a power supply connected to the resistive heating element; and
   means for inducing an oscillatory flow of thermally conductive medium past the resistive heating element in two directions.

10. A thermal ablation system as in claim 9, further comprising:
an introducer sheath having a proximal end, a distal end, an axial lumen for receiving the elongate member of the catheter, and an expandable cage at its distal end, wherein the expandable cage will surround the heating element when the catheter is in place in the axial lumen of the sheath.

11. A thermal ablation system as in claim 10, further comprising at least one temperature sensing element on the expandable cage.

12. A thermal ablation system as in claim 11, wherein the temperature sensing element is at a point of maximum radial expansion on the expandable cage.

13. A thermal ablation system as in claim 9, wherein the means for inducing an oscillatory flow includes:
an oscillatory pump connected to a proximal end of the lumen in the elongate member.

14. A thermal ablation system as in claim 13, wherein the oscillatory pump is a syringe connected to the lumen of the elongate member.

15. A thermal ablation system as in claim 9, wherein the resistive heating element comprises a coil having spaced-apart windings and the catheter further includes means for suspending the coil away from an exterior surface of the elongate member to form a circulation region between the surface and the coil.

16. A thermal ablation system as in claim 15, wherein the means for suspending the coil comprises three or more axial ribs formed along the distal end of the elongate member with trough regions between adjacent ribs defining the circulation regions.

17. A method for ablating a hollow body organ, said method comprising:
percutaneously introducing a catheter into the interior of said hollow body organ, said catheter having a heating element and fluid distributing means at its distal end, wherein the heating element is directly exposed to fluid within the organ;
introducing a thermally conductive medium into the hollow body organ through the fluid distributing means so that the medium is unconstrained and in direct thermal contact with the interior wall of the organ;
heating the thermally conductive medium within the hollow body organ using the heating element; and
alternately aspirating and expelling volumes of thermally conductive medium through the fluid distributing means past the heating element in a reversing flow pattern with substantially all the aspirated medium and all the expelled medium flowing past the heating element to effect mixing of the fluid and increase heat flux and uniformity of temperature distribution.

18. A method as in claim 17, further comprising:
expanding a cage structure within the hollow body organ; and
positioning the heating element of the catheter within the expanded cage structure prior to heating the thermally conductive medium.

19. A method as in claim 18, further comprising sensing the temperature using at least one sensor disposed on the expanded cage structure.

20. A method as in claim 19, wherein the sensor is located at a point of maximum radial expansion on the expandable cage structure.

21. A method as in claim 17, wherein the aspirating and expelling steps are effected with a syringe connected to the fluid distributing means.

22. A method as in claim 17, wherein the volumes which are aspirated and expelled are in the range from 0.1 ml to 3 ml.

23. A method as in claim 17, wherein the volumes are aspirated and expelled at a frequency in the range from 0.01 to 5 Hz.

24. A method as in claim 17, wherein the preselected temperature is in the range from 45° C. to 70° C.

25. A method as in claim 17, wherein the hollow body organ is the gallbladder, the temperature is in the range from 50° C. to 65° C., the frequency of aspiration and expelling is from 0.1 Hz to 5 Hz, the volumes are in the range from 0.1 ml to 3 ml, and the total treatment time is from 15 minutes to 45 minutes.

26. A thermal ablation catheter comprising:
an elongate member having a proximal end, a distal end, and a lumen extending between said proximal and distal ends;
a heating element disposed over a predetermined length of the distal end of the elongate member;
means for suspending the heating element away from an exterior surface of the elongate member to form a circulation region between the surface and the heating element, wherein the means for suspending comprises three or more axial ribs formed along the distal end of the elongate member with trough regions between adjacent ribs defining the circulation region; and
means for distributing a heat transfer fluid from the lumen to the region between the member surface and the heating element.

27. A thermal ablation catheter as is in claim 26, wherein the elongate member is at least partly flexible.

28. A thermal ablation catheter as in claim 26, wherein the heating element is a coil having spaced-apart windings.

29. A thermal ablation catheter as in claim 26, wherein the means for distributing a heat transfer fluid comprises a plurality of ports in the elongate member opening into the trough regions.

30. A thermal ablation catheter as in claim 29, wherein the heating element is a coiled wire having a diameter in the range from about 0.05 mm to 0.25 mm, wherein adjacent windings of the coil are spaced-apart by from 0.5 to 2 wire diameters to permit free flow of heat transfer fluid through the heating element.

31. A thermal ablation catheter as in claim 26, further comprising a cage structure surrounding the heating element and means for expanding the cage structure at the distal end of the elongate member.

32. A thermal ablation catheter as in claim 31, wherein the means for expanding a cage is an introducer sheath having a proximal end, a distal end, and the expandable cage at its distal end.

33. A thermal ablation system comprising:
a catheter including an elongate member adapted for insertion into a hollow body cavity; said elongate member having proximal and distal ends and a resistive heating element having spaced-apart windings mounted on an exterior surface at the distal end of the elongate member;
means for suspending the coil away from an exterior surface of the elongate member to form a circulation region between the surface and the coil;

a power supply connected to the resistive heating element; and means for inducing an oscillatory flow of thermally conductive medium past the resistive heating element.

34. A thermal ablation system as in claim 33, further comprising:

an introducer sheath having a proximal end, a distal end, and an axial lumen for receiving the elongate member of the catheter, and an expandable cage at its distal end, wherein the expandable cage will surround the heating element when the catheter is in place in the axial lumen of the sheath.

35. A thermal ablation system as in claim 34, further comprising at least one temperature sensing element on the expandable cage.

36. A thermal ablation system as in claim 35, wherein the temperature sensing element is at a point of maximum radial expansion on the expandable cage.

37. A thermal ablation system as in claim 33, wherein the means for inducing an oscillatory flow includes:

a lumen extending from the proximal end to the distal end of the elongate member;

an oscillatory pump connected to the proximal end of the lumen; and a plurality of ports in the elongate member opening from the lumen and through the heating element.

38. A thermal ablation system as in claim 37, wherein the oscillatory pump is a syringe connected to the lumen of the elongate member.

39. A thermal ablation system as in claim 33, wherein the means for suspending the coil comprises three or more axial ribs formed along the distal end of the elongate member with trough regions between adjacent ribs defining the circulation regions.

40. A method for ablating a hollow body organ, said method comprising:

percutaneously introducing a catheter into the interior of said hollow body organ, said catheter having a heating element and fluid distributing means at its distal end, wherein the heater element is directly exposed to fluid within the organ;

expanding a cage structure within the hollow body organ;

positioning the heating element of the catheter within the expanded cage structure;

introducing a thermally conductive medium into the hollow body organ through the fluid distributing means so that the medium is unconstrained and in direct thermal contact with the interior wall of the organ;

heating the thermally conductive medium within the hollow body organ using the heating element; and alternately aspirating and expelling volumes of thermally conductive medium through the fluid distributing means to effect mixing of the fluid and increase heat flux and uniformity of temperature distribution.

41. A method as in claim 40, further comprising sensing the temperature using at least one sensor disposed on the expanded cage structure.

42. A method as in claim 41, wherein the sensor is located at a point of maximum radial expansion on the expandable cage structure.

43. A method as in claim 40, wherein the aspirating and expelling steps are effected with a syringe connected to the fluid distributing means.

44. A method as in claim 40, wherein the volumes which are aspirated and expelled are in the range from 0.1 ml to 3 ml.

45. A method as in claim 40, wherein the volumes are aspirated and expelled at a frequency in the range from 0.01 to 5 Hz.

46. A method as in claim 40, wherein the preselected temperature is in the range from 45° C. to 70° C.

47. A method as in claim 40, wherein the hollow body organ is the gallbladder, the temperature is in the range from 50° C. to 65° C., the frequency of aspiration and expelling is from 0.1 Hz to 5 Hz, the volumes are in the range from 0.1 ml to 3 ml, and the total treatment time is from 15 minutes to 45 minutes.

48. A method for ablating a hollow body organ, said method comprising:

percutaneously introducing a catheter into the interior of said hollow body organ, said catheter having a heating element and fluid distributing means at its distal end, wherein the heater element is directly exposed to fluid within the organ and the fluid distributing means directs fluid generally radially through the heating element;

introducing a thermally conductive medium into the hollow body organ through the fluid distributing means so that the medium is unconstrained and in direct thermal contact with the interior wall of the organ;

heating the thermally conductive medium within the hollow body organ using the heating element; and alternately aspirating and expelling volumes of thermally conductive medium through the fluid distributing means to effect mixing of the fluid and increase heat flux and uniformity of temperature distribution.

49. A method as in claim 48, further comprising:

expanding a cage structure within the hollow body organ; and positioning the heating element of the catheter within the expanded cage structure prior to heating the thermally conductive medium.

50. A method as in claim 49, further comprising sensing the temperature using at least one sensor disposed on the expanded cage structure.

51. A method as in claim 50, wherein the sensor is located at a point of maximum radial expansion on the expandable cage structure.

52. A method as in claim 48, wherein the aspirating and expelling steps are effected with a syringe connected to the fluid distributing means.

53. A method as in claim 48, wherein the volumes which are aspirated and expelled are in the range from 0.1 ml to 3 ml.

54. A method as in claim 48, wherein the volumes are aspirated and expelled at a frequency in the range from 0.01 to 5 Hz.

55. A method as in claim 48, wherein the preselected temperature is in the range from 45° C. to 70° C.

56. A method as in claim 48, wherein the hollow body organ is the gallbladder, the temperature is in the range from 50° C. to 65° C., the frequency of aspiration and expelling is from 0.1 Hz to 5 Hz, the volumes are in the range from 0.1 ml to 3 ml, and the total treatment time is from 15 minutes to 45 minutes.

57. A method for ablating a hollow body organ, said method comprising:

introducing a catheter into the interior of said hollow body organ;

introducing a thermally conductive medium into the hollow body organ so that the medium is unconstrained and in direct thermal conduct with the interior wall of the organ; and alternately aspirating and expelling volumes of the thermally conductive medium through the catheter and past a heating element in a reversing flow pattern with substantially all the aspirated medium and all the expelled medium flowing past the heating element to effect mixing of the fluid and increase heat flux and uniformity of temperature distribution.

58. A method as in claim 57, wherein the catheter is introduced percutaneously.

59. A method as in claim 57, wherein the thermally conductive medium is introduced through the catheter.

60. A method as in claim 57, wherein the heating element is on the distal end of the catheter.

* * * * *